US012636312B2

(12) United States Patent
Sun

(10) Patent No.: US 12,636,312 B2
(45) Date of Patent: May 26, 2026

(54) GOLD CLUSTERS (AuCs), COMPOSITION AND METHOD FOR TREATMENT OF LIVER CIRRHOSIS

(71) Applicant: Wuhan Vast Conduct Science Foundation CO., LTD., Wuhan (CN)

(72) Inventor: Taolei Sun, Wuhan (CN)

(73) Assignee: Wuhan Vast Conduct Science Foundation CO., LTD., Wuhan (CN)

( * ) Notice: Subject to any disclaimer, the term of this patent is extended or adjusted under 35 U.S.C. 154(b) by 836 days.

(21) Appl. No.: 17/758,308

(22) PCT Filed: Oct. 28, 2020

(86) PCT No.: PCT/CN2020/124285
§ 371 (c)(1),
(2) Date: Jul. 1, 2022

(87) PCT Pub. No.: WO2021/184762
PCT Pub. Date: Sep. 23, 2021

(65) Prior Publication Data
US 2023/0037702 A1 Feb. 9, 2023

Related U.S. Application Data

(63) Continuation-in-part of application No. PCT/CN2020/079499, filed on Mar. 16, 2020.

(30) Foreign Application Priority Data

Mar. 16, 2020 (WO) ................ PCT/CN2020/079499

(51) Int. Cl.
A61K 33/242 (2019.01)
A61K 47/18 (2017.01)
A61P 1/16 (2006.01)

(52) U.S. Cl.
CPC .......... *A61K 33/242* (2019.01); *A61K 47/183* (2013.01); *A61P 1/16* (2018.01)

(58) Field of Classification Search
CPC .. A61K 33/242; A61K 47/183; A61K 47/542; A61K 47/6923; A61K 47/6929; A61K 47/64; A61P 1/16; Y02A 50/30
See application file for complete search history.

(56) References Cited

U.S. PATENT DOCUMENTS

2018/0036270 A1    2/2018    Stokes
2018/0169044 A1    6/2018    Hamill et al.

FOREIGN PATENT DOCUMENTS

WO    2013176468    11/2013
WO    2018024111    2/2018
WO    2018095429    5/2018

OTHER PUBLICATIONS

English translation of WO2018/024111 retrieved from Espacenet on Apr. 15, 2025.*
Plaza et al. (2018) Effects of the Usage of L-Cysteine (L-Cys) on Human Health. Molecules. 23: 575.

* cited by examiner

*Primary Examiner* — Jessica Worsham
(74) *Attorney, Agent, or Firm* — Yihe Intellectual Property Service Company, Ltd; George Liu

(57) ABSTRACT

Ligand-bound gold clusters and compositions comprising the ligand-bound gold clusters are used for treating liver cirrhosis and manufacturing a medicament for treatment of liver cirrhosis. Methods for treating liver cirrhosis.

7 Claims, 15 Drawing Sheets

GOLD CLUSTERS (AuCs), COMPOSITION AND METHOD FOR TREATMENT OF LIVER CIRRHOSIS

CROSS-REFERENCE TO RELATED APPLICATIONS

This application is a National Phase Entry of International Application No. PCT/CN2020/124285, filed Oct. 28, 2020, which claims benefit of International Application No. PCT/CN2020/079499, filed Mar. 16, 2020; all of these applications are incorporated herein by reference.

FIELD OF THE INVENTION

The present invention relates to the technical field of treatment of liver cirrhosis, particularly to ligand-bound gold clusters (AuCs), composition comprising the ligand-bound AuCs, and methods employing ligand-bound AuCs for treatment of liver cirrhosis.

BACKGROUND OF THE INVENTION

The liver is the largest solid organ in a human body, and performs many important functions including: making blood proteins that aid in clotting, transporting oxygen, and helping the immune system; storing excess nutrients and returning some of the nutrients to the bloodstream; manufacturing bile to help digest food; helping the body store sugar (glucose) in the form of glycogen; ridding the body of harmful substances in the bloodstream, including drugs and alcohol; and breaking down saturated fat and producing cholesterol.

Liver cirrhosis is a slowly progressive disease, being developed over many years due to long-term, continuous damage to the liver. Along with the development of liver cirrhosis, healthy liver tissue is gradually destroyed and replaced by scar tissue. The scar tissue blocks the flow of blood through the liver and slows the liver's ability to process nutrients, hormones, drugs, and natural toxins. It also reduces the production of proteins and other substances made by the liver. Cirrhosis may eventually lead to liver failure that may require a liver transplant and/or liver cancer.

In the early stage of liver cirrhosis, there are no obvious symptoms due to strong liver compensatory function. In its later stage, the symptoms include liver function damage, portal hypertension, upper gastrointestinal bleeding, hepatic encephalopathy, secondary infection, spleen hyperfunction, ascites, canceration and other complications. Liver cirrhosis results from gradual liver deformation and hardening. Histopathologically, liver cirrhosis is characterized by extensive hepatic cell necrosis, nodular regeneration of residual hepatocytes, connective tissue hyperplasia and fibrous septum formation, leading to the destruction of hepatic lobular structure and the formation of pseudolobules.

Liver cirrhosis has different causes. Some people with cirrhosis have more than one cause of liver damage. The common causes of cirrhosis include long-term alcohol abuse, chronic hepatitis B and C infection, fatty liver disease, toxic metals, genetic diseases, nutrition disorders, industrial poisons, drugs, circulation disorders, metabolic disorders, cholestasis, schistosomiasis, etc.

Liver cirrhosis could be diagnosed by many tests/techniques. For example, blood test could suggest liver cirrhosis if the levels of the liver enzymes including alanine transaminase (ALT), aspartate transaminase (AST) and alkaline phosphatase (ALP), and bilirubin are increased and the levels of blood proteins are decreased.

Currently, while treatments can delay the progress of liver cirrhosis by dealing with its causes, there is no specific treatments for liver cirrhosis.

SUMMARY OF THE INVENTION

The present invention provides the use of ligand-bound gold clusters to treat liver cirrhosis in a subject, the method of treating liver cirrhosis in a subject with ligand-bound gold clusters, and the use of ligand-bound gold clusters for manufacture of medicament for treatment of liver cirrhosis in a subject.

Certain embodiments of the present invention use of a ligand-bound gold cluster to treat liver cirrhosis in a subject, wherein the ligand-bound gold cluster comprises a gold core; and a ligand bound to the gold core.

In certain embodiments of the treatment use, the gold core has a diameter in the range of 0.5-3 nm. In certain embodiments, the gold core has a diameter in the range of 0.5-2.6 nm.

In certain embodiments of the treatment use, the ligand is one selected from the group consisting of L-cysteine and its derivatives, D-cysteine and its derivatives, cysteine-containing oligopeptides and their derivatives, and other thiol-containing compounds.

In certain embodiments of the treatment use, the L-cysteine and its derivatives are selected from the group consisting of L-cysteine, N-isobutyryl-L-cysteine (L-NIBC), and N-acetyl-L-cysteine (L-NAC), and the D-cysteine and its derivatives are selected from the group consisting of D-cysteine, N-isobutyryl-D-cysteine (D-NIBC), and N-acetyl-D-cysteine (D-NAC).

In certain embodiments of the treatment use, the cysteine-containing oligopeptides and their derivatives are cysteine-containing dipeptides, cysteine-containing tripeptides or cysteine-containing tetrapeptides.

In certain embodiments of the treatment use, the cysteine-containing dipeptides are selected from the group consisting of L(D)-cysteine-L(D)-arginine dipeptide (CR), L(D)-arginine-L(D)-cysteine dipeptide (RC), L(D)-histidine-L(D)-cysteine dipeptide (HC), and L(D)-cysteine-L(D)-histidine dipeptide (CH).

In certain embodiments of the treatment use, the cysteine-containing tripeptides are selected from the group consisting of glycine-L(D)-cysteine-L(D)-arginine tripeptide (GCR), L(D)-proline-L(D)-cysteine-L(D)-arginine tripeptide (PCR), L(D)-lysine-L(D)-cysteine-L(D)-proline tripeptide (KCP), and L(D)-glutathione (GSH).

In certain embodiments of the treatment use, the cysteine-containing tetrapeptides are selected from the group consisting of glycine-L(D)-serine-L(D)-cysteine-L(D)-arginine tetrapeptide (GSCR), and glycine-L(D)-cysteine-L(D)-serine-L(D)-arginine tetrapeptide (GCSR).

In certain embodiments of the treatment use, the other thiol-containing compounds are selected from the group consisting of 1-[(2S)-2-methyl-3-thiol-1-oxopropyl]-L(D)-proline, thioglycollic acid, mercaptoethanol, thiophenol, D-3-trolovol, N-(2-mercaptopropionyl)-glycine, and dodecyl mercaptan.

Certain embodiments of the present invention use a ligand-bound gold cluster for manufacture of a medicament for the treatment of liver cirrhosis in a subject, wherein ligand-bound gold cluster comprises a gold core; and a ligand bound the gold core.

In certain embodiments of the manufacture use, the gold core has a diameter in the range of 0.5-3 nm. In certain embodiments, the gold core has a diameter in the range of 0.5-2.6 nm.

In certain embodiments of the manufacture use, the ligand is one selected from the group consisting of L-cysteine and its derivatives, D-cysteine and its derivatives, cysteine-containing oligopeptides and their derivatives, and other thiol-containing compounds.

In certain embodiments of the manufacture use, the L-cysteine and its derivatives are selected from the group consisting of L-cysteine, N-isobutyryl-L-cysteine (L-NIBC), and N-acetyl-L-cysteine (L-NAC), and the D-cysteine and its derivatives are selected from the group consisting of D-cysteine, N-isobutyryl-D-cysteine (D-NIBC), and N-acetyl-D-cysteine (D-NAC).

In certain embodiments of the manufacture use, the cysteine-containing oligopeptides and their derivatives are cysteine-containing dipeptides, cysteine-containing tripeptides or cysteine-containing tetrapeptides.

In certain embodiments of the manufacture use, the cysteine-containing dipeptides are selected from the group consisting of L(D)-cysteine-L(D)-arginine dipeptide (CR), L(D)-arginine-L(D)-cysteine dipeptide (RC), L(D)-histidine-L(D)-cysteine dipeptide (HC), and L(D)-cysteine-L(D)-histidine dipeptide (CH).

In certain embodiments of the manufacture use, the cysteine-containing tripeptides are selected from the group consisting of glycine-L(D)-cysteine-L(D)-arginine tripeptide (GCR), L(D)-proline-L(D)-cysteine-L(D)-arginine tripeptide (PCR), L(D)-lysine-L(D)-cysteine-L(D)-proline tripeptide (KCP), and L(D)-glutathione (GSH).

In certain embodiments of the manufacture use, the cysteine-containing tetrapeptides are selected from the group consisting of glycine-L(D)-serine-L(D)-cysteine-L(D)-arginine tetrapeptide (GSCR), and glycine-L(D)-cysteine-L(D)-serine-L(D)-arginine tetrapeptide (GC SR).

In certain embodiments of the manufacture use, the other thiol-containing compounds are selected from the group consisting of 1-[(2S)-2-methyl-3-thiol-1-oxopropyl]-L(D)-proline, thioglycollic acid, mercaptoethanol, thiophenol, D-3-trolovol, N-(2-mercaptopropionyl)-glycine, and dodecyl mercaptan.

The objectives and advantages of the invention will become apparent from the following detailed description of preferred embodiments thereof in connection with the accompanying drawings.

DESCRIPTION OF THE DRAWINGS

Preferred embodiments according to the present invention will now be described with reference to the Figures, in which like reference numerals denote like elements.

DETAILED DESCRIPTION OF THE EMBODIMENTS

Figure 1:
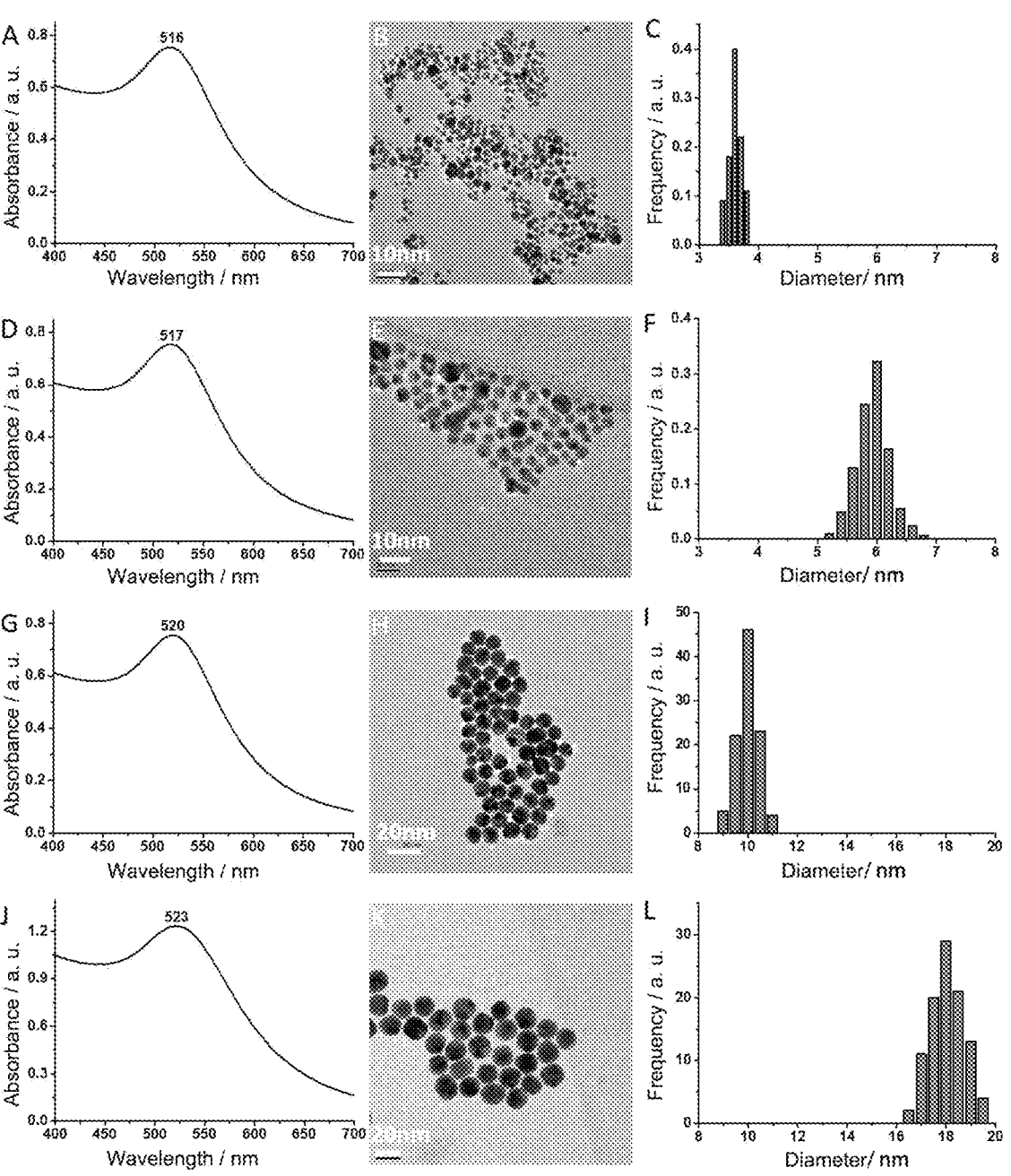
FIG. 1 shows ultraviolet-visible (UV) spectrums, transmission electron microscope (TEM) images and particle size distribution diagrams of ligand L-NIBC-modified gold nanoparticles (L-NIBC-AuNPs) with different particle sizes.

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

Gold clusters (AuCs) are a special form of gold existing between gold atoms and gold nanoparticles. AuCs have a size smaller than 3 nm, and are composed of only several to a few hundreds of gold atoms, leading to the collapse of face-centered cubic stacking structure of gold nanoparticles. As a result, AuCs exhibit molecule-like discrete electronic structures with distinct HOMO-LUMO gap unlike the continuous or quasi-continuous energy levels of gold nanoparticles. This leads to the disappearance of surface plasmon resonance effect and the corresponding plasmon resonance absorption band (520±20 nm) at uv-vis spectrum that possessed by conventional gold nanoparticles.

The present invention provides a ligand-bound AuC.

In certain embodiments, the ligand-bound AuC comprises a ligand and a gold core, wherein the ligand is bound to the gold core. The binding of ligands with gold cores means that ligands form stable-in-solution complexes with gold cores through covalent bond, hydrogen bond, electrostatic force, hydrophobic force, van der Waals force, etc In certain embodiments, the diameter of the gold core is in the range of 0.5-3 nm. In certain embodiments, the diameter of the gold core is in the range of 0.5-2.6 nm.

In certain embodiments, the ligand of the ligand-bound AuC is a thiol-containing compound or oligopeptide. In certain embodiments, the ligand bonds to the gold core to form a ligand-bonded AuC via Au—S bond.

In certain embodiments, the ligand is, but not limited to, L-cysteine, D-cysteine, or a cysteine derivative. In certain embodiments, the cysteine derivative is N-isobutyryl-L-cysteine (L-NIBC), N-isobutyryl-D-cysteine (D-NIBC), N-acetyl-L-cysteine (L-NAC), or N-acetyl-D-cysteine (D-NAC).

In certain embodiments, the ligand is, but not limited to, a cysteine-containing oligopeptide and its derivatives. In certain embodiments, the cysteine-containing oligopeptide is a cysteine-containing dipeptide. In certain embodiments, the cysteine-containing dipeptide is L(D)-cysteine-L(D)-arginine dipeptide (CR), L(D)-arginine-L(D)-cysteine dipeptide (RC), or L(D)-cysteine-L-histidine dipeptide (CH). In certain embodiments, the cysteine-containing oligopeptide is a cysteine-containing tripeptide. In certain embodiments, the cysteine-containing tripeptide is glycine-L(D)-cysteine-L(D)-arginine tripeptide (GCR), L(D)-proline-L(D)-cysteine-L(D)-arginine tripeptide (PCR), or L(D)-glutathione (GSH). In certain embodiments, the cysteine-containing oligopeptide is a cysteine-containing tetrapeptide. In certain embodiments, the cysteine-containing tetrapeptide is glycine-L(D)-serine-L(D)-cysteine-L(D)-arginine tetrapeptide (GSCR) or glycine-L(D)-cysteine-L(D)-serine-L(D)-arginine tetrapeptide (GCSR).

In certain embodiments, the ligand is a thiol-containing compound. In certain embodiments, thiol-containing compound is 1-[(2 S)-2-methyl-3-thiol-1-oxopropyl]-L(D)-proline, thioglycollic acid, mercaptoethanol, thiophenol, D-3-trolovol, or dodecyl mercaptan.

The present invention provides a pharmaceutical composition for the treatment of liver cirrhosis in a subject. In certain embodiments, the subject is human. In certain embodiments, the subject is a pet animal such as a dog.

In certain embodiments, the pharmaceutical composition comprises a ligand-bound AuC as disclosed above and a pharmaceutically acceptable excipient. In certain embodiments, the excipient is phosphate-buffered solution, or physiological saline.

The present invention provides a use of the above disclosed ligand-bound AuCs for manufacturing a medication for the treatment of liver cirrhosis in a subject.

The present invention provides a use of the above disclosed ligand-bound AuCs for treating liver cirrhosis in a subject or a method for treating liver cirrhosis in subject using the above disclosed ligand-bound AuCs. In certain embodiments, the method for treatment comprises administering a pharmaceutically effective amount of ligand-bound AuCs to the subject. The pharmaceutically effective amount can be ascertained by routine in vivo studies.

The following examples are provided for the sole purpose of illustrating the principles of the present invention; they are by no means intended to limit the scope of the present invention.

EMBODIMENTS

Embodiment 1. Preparation of Ligand-Bound AuCs 1.1 Dissolving $HAuCl_4$ in methanol, water, ethanol, n-propanol, or ethyl acetate to get a solution A in which the concentration of $HAuCl_4$ is 0.01~0.03M;

1.2 Dissolving a ligand in a solvent to get a solution B in which the concentration of the ligand is 0.01~0.18M; the ligand includes, but not limited to, L-cysteine, D-cysteine and other cysteine derivatives such as N-isobutyryl-L-cysteine (L-NIBC), N-isobutyryl-D-cysteine (D-NIBC), N-acetyl-L-cysteine (L-NAC), and N-acetyl-D-cysteine (D-NAC), cysteine-containing oligopeptides and their derivatives including, but not limited to, dipeptides, tripeptide, tetrapeptide and other peptides containing cysteine, such as L(D)-cysteine-L(D)-arginine dipeptide (CR), L(D)-arginine-L(D)-cysteine dipeptide (RC), L(D)-cysteine L(D)-histidine (CH), glycine-L(D)-cysteine-L(D)-arginine tripeptide (GCR), L(D)-proline-L(D)-cysteine-L(D)-arginine tripeptide (PCR), L(D)-glutathione (GSH), glycine-L(D)-serine-L(D)-cysteine-L(D)-arginine tetrapeptide (GSCR) and glycine-L(D)-cysteine-L(D)-serine-L(D)-arginine tetrapeptide (GCSR), and other thiol-containing compounds, such as one or more of 1-[(2S)-2-methyl-3-thiol-1-oxopropyl]-L(D)-proline, thioglycollic acid, mercaptoethanol, thiophenol, D-3-trolovol and dodecyl mercaptan; the solvent is one or more of methanol, ethyl acetate, water, ethanol, n-propanol, pentane, formic acid, acetic acid, diethyl ether, acetone, anisole, 1-propanol, 2-propanol, 1-butanol, 2-butanol, pentanol, butyl acetate, tributyl methyl ether, isopropyl acetate, dimethyl sulfoxide, ethyl formate, isobutyl acetate, methyl acetate, 2-methyl-1-propanol and propyl acetate;

1.3 Mixing solution A and solution B so that the mole ratio between $HAuCl_4$ and ligand is 1:(0.01~100), stirring them in an ice bath for 0.1~48 h, adding 0.025~0.8M $NaBH_4$ water, ethanol or methanol solution, continuing to stir in an ice water bath and react for 0.1~12 h. The mole ratio between $NaBH_4$ and ligand is 1:(0.01~100);

1.4 Using MWCO 3K~30K ultrafiltration tubes to centrifuge the reaction solution at 8000~17500 r/min by gradient for 10~100 min after the reaction ends to obtain ligand-bound AuCs precipitate in different average particle sizes. The aperture of the filtration membranes for ultrafiltration tubes of different MWCOs directly decides the size of ligand-bound AuCs that can pass the membranes. This step may be optionally omitted;

1.5 Dissolving the ligand-bound AuCs precipitate in different average particle sizes obtained in step (1.4) in water, putting it in a dialysis bag and dialyzing it in water at room temperature for 1~7 days;

1.6 Freeze-drying ligand-bound AuCs for 12~24 h after dialysis to obtain a powdery or flocculant substance, i.e., ligand-bound AuCs.

As detected, the particle size of the powdery or flocculant substance obtained by the foregoing method is smaller than 3 nm (distributed in 0.5-2.6 nm in general). No obvious absorption peak at 520 nm. It is determined that the obtained powder or floc is ligand-bound AuCs.

Embodiment 2. Preparation and Characterization of
AuCs Bound with Different Ligands 2.1 Preparation of L-NIBC-bound AuCs, i.e. L-NIBC-
AuCs Taking ligand L-NIBC for example, the preparation and
confirmation of AuCs bound with ligand L-NIBC are
detailed.

2.1.1 Weigh 1.00 g of $HAuCl_4$ and dissolve it in 100 mL
of methanol to obtain a 0.03M solution A;

2.1.2 Weigh 0.57 g of L-NIBC and dissolve it in 100 mL
of glacial acetic acid (acetic acid) to obtain a 0.03M solution
B;

2.1.3 Measure 1 mL of solution A, mix it with 0.5 mL, 1
mL, 2 mL, 3 mL, 4 mL, or 5 mL of solution B respectively
(i.e. the mole ratio between $HAuCl_4$ and L-NIBC is 1:0.5,
1:1, 1:2, 1:3, 1:4, 1:5 respectively), react in an ice bath under
stirring for 2 h, quickly add 1 mL of freshly prepared 0.03M
(prepared by weighing 11.3 mg of $NaBH_4$ and dissolving it
in 10 mL of ethanol) $NaBH_4$ ethanol solution when the
solution turns colorless from bright yellow, continue the
reaction for 30 min after the solution turns dark brown, and
add 10 mL of acetone to terminate the reaction.

2.1.4 After the reaction, the reaction solution is subjected
to gradient centrifugation to obtain L-NIBC-AuCs powder
with different particle sizes. Specific method: After the
reaction is completed, the reaction solution is transferred to
an ultrafiltration tube with MWCO of 30K and a volume of
50 mL, and centrifuged at 10000 r/min for 20 min, and the
retentate in the inner tube is dissolved in ultrapure water to
obtain powder with a particle size of about 2.6 nm. Then, the
mixed solution in the outer tube is transferred to an ultra-
filtration tube with a volume of 50 mL and MWCO of 10K,
and centrifuged at 13,000 r/min for 30 min. The retentate in
the inner tube is dissolved in ultrapure water to obtain
powder with a particle size of about 1.8 nm. Then the mixed
solution in the outer tube is transferred to an ultrafiltration
tube with a volume of 50 mL and MWCO of 3K, and
centrifuged at 17,500 r/min for 40 min. The retentate in the
inner tube is dissolved in ultrapure water to obtain powder
with a particle size of about 1.1 nm.

2.1.5 Precipitate the powder in three different particle
sizes obtained by gradient centrifugation, remove the sol-
vent respectively, blow the crude product dry with N2,
dissolve it in 5 mL of ultrapure water, put it in a dialysis bag
(MWCO is 3 KDa), put the dialysis bag in 2 L of ultrapure
water, change water every other day, dialyze it for 7 days,
freeze-dry it and keep it for future use.

2.2 Characterization of L-NIBC-AuCs

Characterization experiment was conducted for the pow-
der obtained above (L-NIBC-AuCs). Meanwhile, ligand
L-NIBC-modified gold nanoparticles (L-NIBC-AuNPs) are
used as control. The method for preparing gold nanoparticles
with ligand being L-NIBC refers to the reference (W. Yan,
L. Xu, C. Xu, W. Ma, H. Kuang, L. Wang and N. A. Kotov,
Journal of the American Chemical Society 2012, 134,
15114; X. Yuan, B. Zhang, Z. Luo, Q. Yao, D. T. Leong, N.
Yan and J. Xie, Angewandte Chemie International Edition
2014, 53, 4623).

2.2.1 Observation of the morphology by transmission
electron microscope (TEM)

The test powders (L-NIBC-AuCs sample and L-NIBC-
AuNPs sample) were dissolved in ultrapure water to 2 mg/L
as samples, and then test samples were prepared by hanging
drop method. More specifically, 5 μL of the samples were
dripped on an ultrathin carbon film, volatized naturally till the water drop disappeared, and then observe the morphol-
ogy of the samples by JEM-2100F STEM/EDS field emis-
sion high-resolution TEM.

Figure 2:
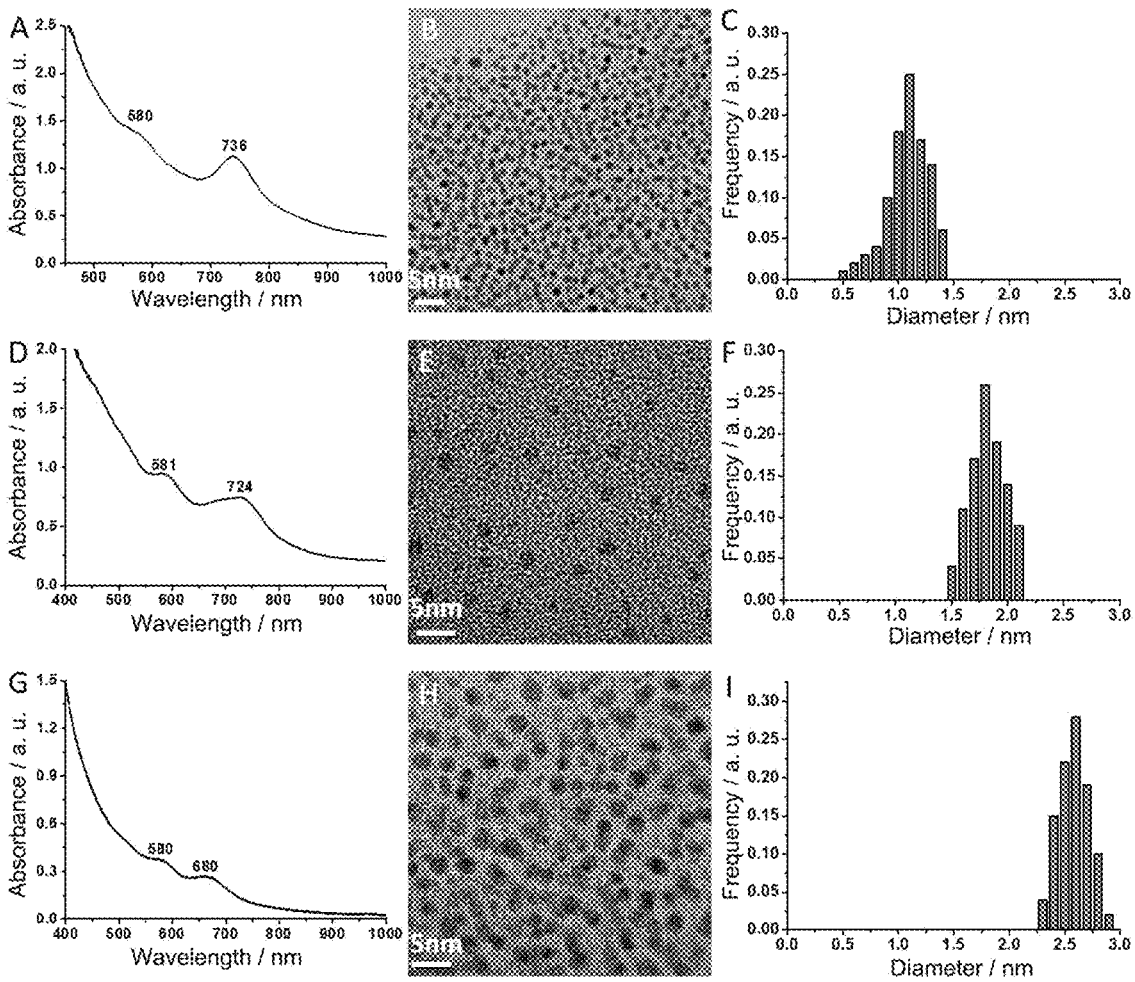
FIG. 2 shows ultraviolet-visible (UV) spectrums, TEM images and particle size distribution diagrams of ligand L-NIBC-bound gold clusters (L-NIBC-AuCs) with different particle sizes.

The four TEM images of L-NIBC-AuNPs are shown in
panels B, E, H, and K of FIG. 1; the three TEM images of
L-NIBC-AuCs are shown in panels B, E, and H of FIG. 2.

The images in FIG. 2 indicate that each of L-NIBC-AuCs
samples has a uniform particle size and good dispersibility,
and the average diameter of L-NIBC-AuCs (refer to the
diameter of gold core) is 1.1 nm, 1.8 nm and 2.6 nm
respectively, in good accordance with the results in panels C,
F and I of FIG. 2. In comparison, L-NIBC-AuNPs samples
have a larger particle size. Their average diameter (refer to
the diameter of gold core) is 3.6 nm, 6.0 nm, 10.1 nm and
18.2 nm respectively, in good accordance with the results in
panels C, F, I and L of FIG. 1.

2.2.2 Ultraviolet (UV)-visible (vis) absorption spectra

The test powders (L-NIBC-AuCs sample and L-NIBC-
AuNPs sample) were dissolved in ultrapure water till the
concentration was 10 $mg \cdot L^{-1}$, and the UV-vis absorption
spectra were measured at room temperature. The scanning
range was 190-1100 nm, the sample cell was a standard
quartz cuvette with an optical path of 1 cm, and the reference
cell was filled with ultrapure water.

The UV-vis absorption spectra of the four L-NIBC-
AuNPs samples with different sizes are shown in panels A,
D, G and J of FIG. 1, and the statistical distribution of
particle size is shown in panels C, F, I and L of FIG. 1; the
UV-vis absorption spectra of three L-NIBC-AuCs samples
with different sizes are shown in panels A, D and G of FIG.
2, and the statistical distribution of particle size is shown in
panels C, F and I of FIG. 2.

FIG. 1 indicates that due to the surface plasmon effect,
L-NIBC-AuNPs had an absorption peak at about 520 nm.
The position of the absorption peak is relevant with particle
size. When the particle size is 3.6 nm, the UV absorption
peak appears at 516 nm; when the particle size is 6.0 nm, the
UV absorption peak appears at 517 nm; when the particle
size is 10.1 nm, the UV absorption peak appears at 520 nm,
and when the particle size is 18.2 nm, the absorption peak
appears at 523 nm. None of the four samples has any
absorption peak above 560 nm.

FIG. 2 indicates that in the UV absorption spectra of three
L-NIBC-AuCs samples with different particle sizes, the
surface plasmon effect absorption peak at 520 nm disap-
peared, and two obvious absorption peaks appeared above
560 nm and the positions of the absorption peaks varied
slightly with the particle sizes of AuCs. This is because
AuCs exhibit molecule-like properties due to the collapse of
the face-centered cubic structure, which leads to the discon-
tinuity of the density of states of AuCs, the energy level
splitting, the disappearance of plasmon resonance effect and
the appearance of a new absorption peak in the long-wave
direction. It could be concluded that the three powder
samples in different particle sizes obtained above are all
ligand-bound AuCs.

2.2.3 Fourier transform infrared spectroscopy

Infrared spectra were measured on a VERTEX80V Fou-
rier transform infrared spectrometer manufactured by
Bruker in a solid powder high vacuum total reflection mode.
The scanning range is 4000-400 $cm^{-1}$ and the number of
scans is 64. Taking L-NIBC-AuCs samples for example, the
test samples were L-NIBC-AuCs dry powder with three
different particle sizes and the control sample was pure
L-NIBC powder. The results are shown in FIG. 3.

Figure 3:
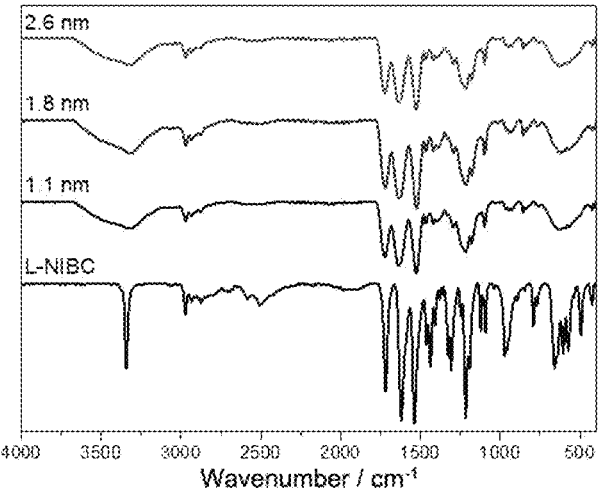
FIG. 3 shows infrared spectra of L-NIBC-AuCs with different particle sizes.

FIG. 3 shows the infrared spectrum of L-NIBC-AuCs
with different particle sizes. Compared with pure L-NIBC (the curve at the bottom), the S—H stretching vibrations of L-NIBC-AuCs with different particle sizes all disappeared completely at 2500-2600 cm$^{-1}$, while other characteristic peaks of L-NIBC were still observed, proving that L-NIBC molecules were successfully bound to the surface of AuCs via Au—S bond. The figure also shows that the infrared spectrum of the ligand-bound AuCs is irrelevant with its size.

AuCs bound with other ligands were prepared by a method similar to the above method, except that the solvent of solution B, the feed ratio between HAuCl$_4$ and ligand, the reaction time and the amount of NaBH$_4$ added were slightly adjusted. For example: when L-cysteine, D-cysteine, N-isobutyryl-L-cysteine (L-NIBC) or N-isobutyryl-D-cysteine (D-NIBC) is used as the ligand, acetic acid is selected as the solvent; when dipeptide CR, dipeptide RC or 1-[(2S)-2-methyl-3-thiol-1-oxopropyl]-L-proline is used as the ligand, water is selected as the solvent, and so on and so forth; other steps are similar, so no further details are provided herein.

The present invention prepared and obtained a series of ligand-bound AuCs by the foregoing method. The ligands and the parameters of the preparation process are shown in Table 1.

Figure 4:
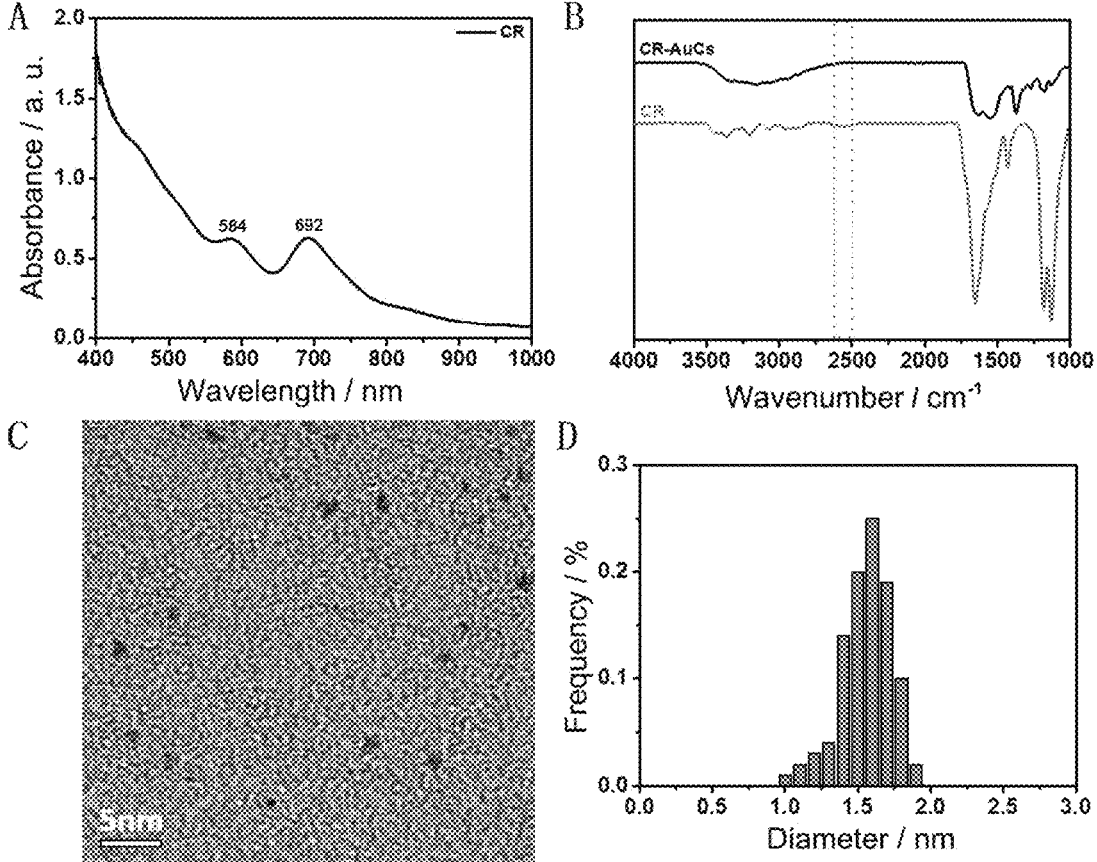
FIG. 4 shows UV, infrared, TEM, and particle size distribution diagrams of ligand CR-bound gold clusters (CR-AuCs).
Figure 5:
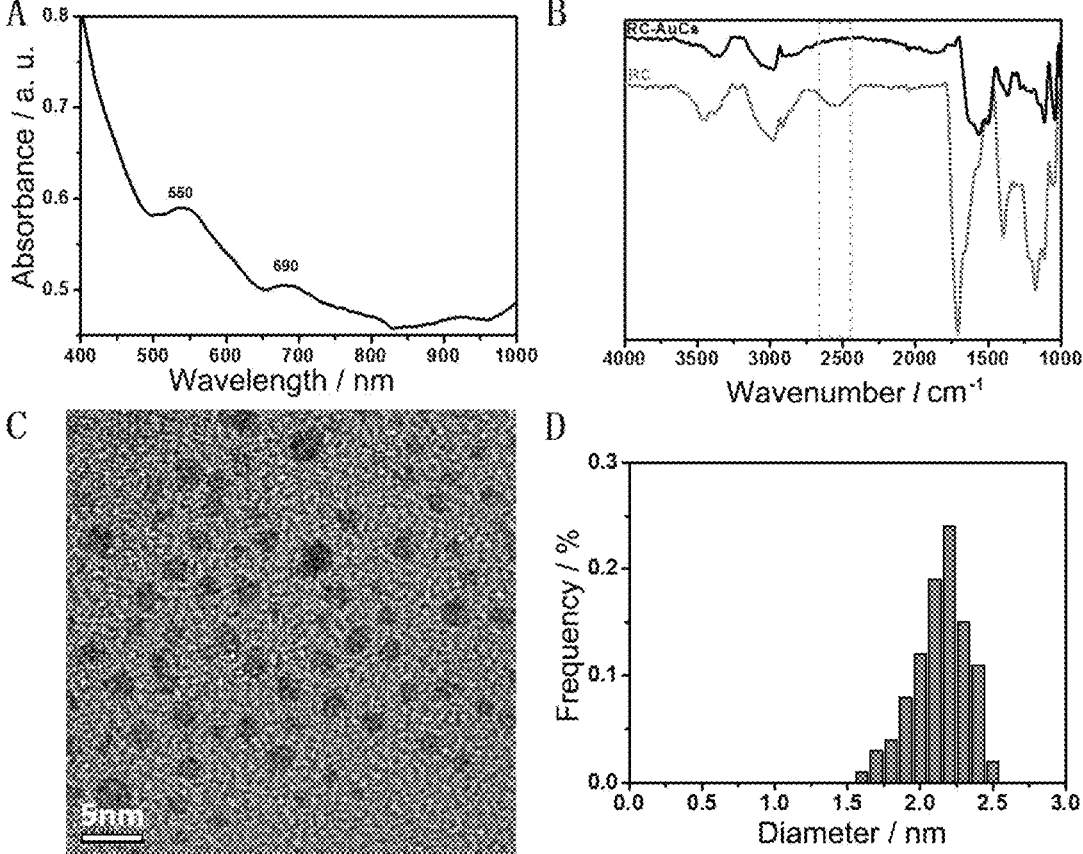
FIG. 5 shows UV, infrared, TEM, and particle size distribution diagrams of ligand RC-bound gold clusters (RC-AuCs).
Figure 6:
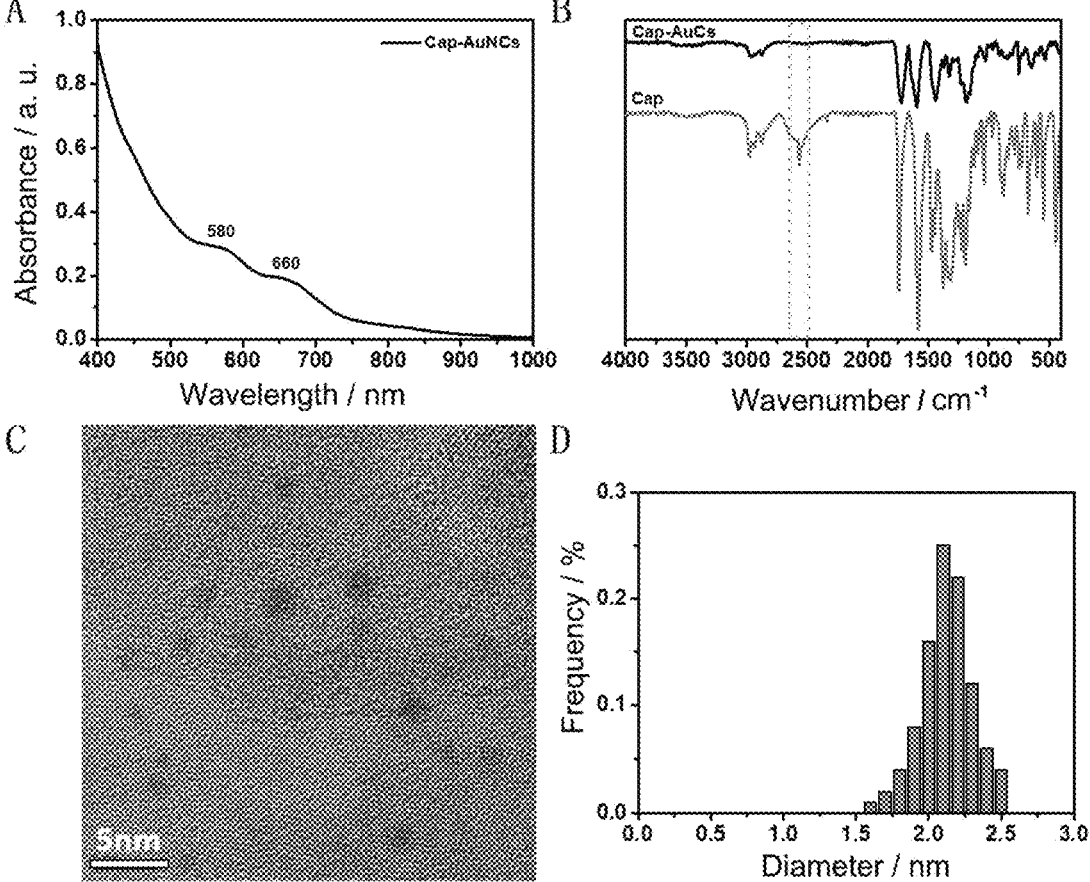
FIG. 6 shows UV, infrared, TEM, and particle size distribution diagrams of ligand 1-[(2S)-2-methyl-3-thiol-1-oxopropyl]-L-proline (i.e., Cap)-bound gold clusters (Cap-AuCs).
Figure 7:
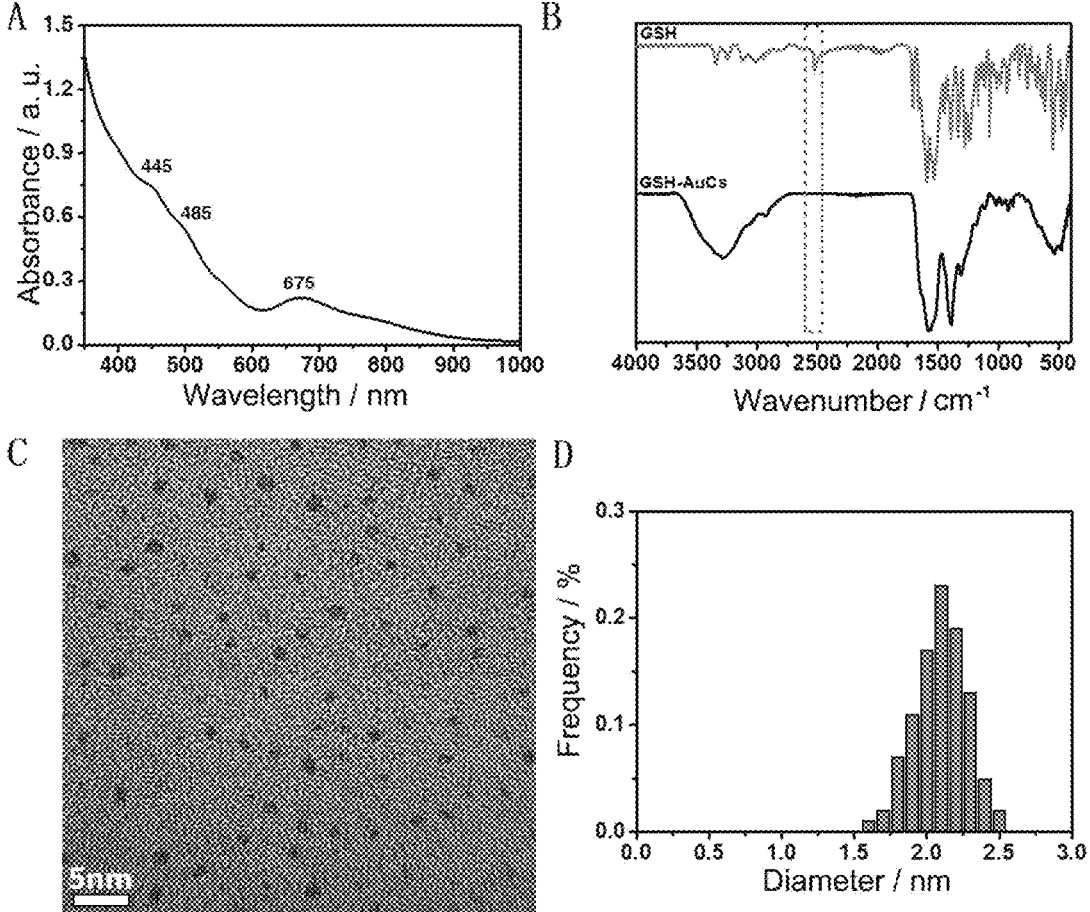
FIG. 7 shows UV, infrared, TEM, and particle size distribution diagrams of ligand GSH-bound gold clusters (GSH-AuCs).
Figure 8:
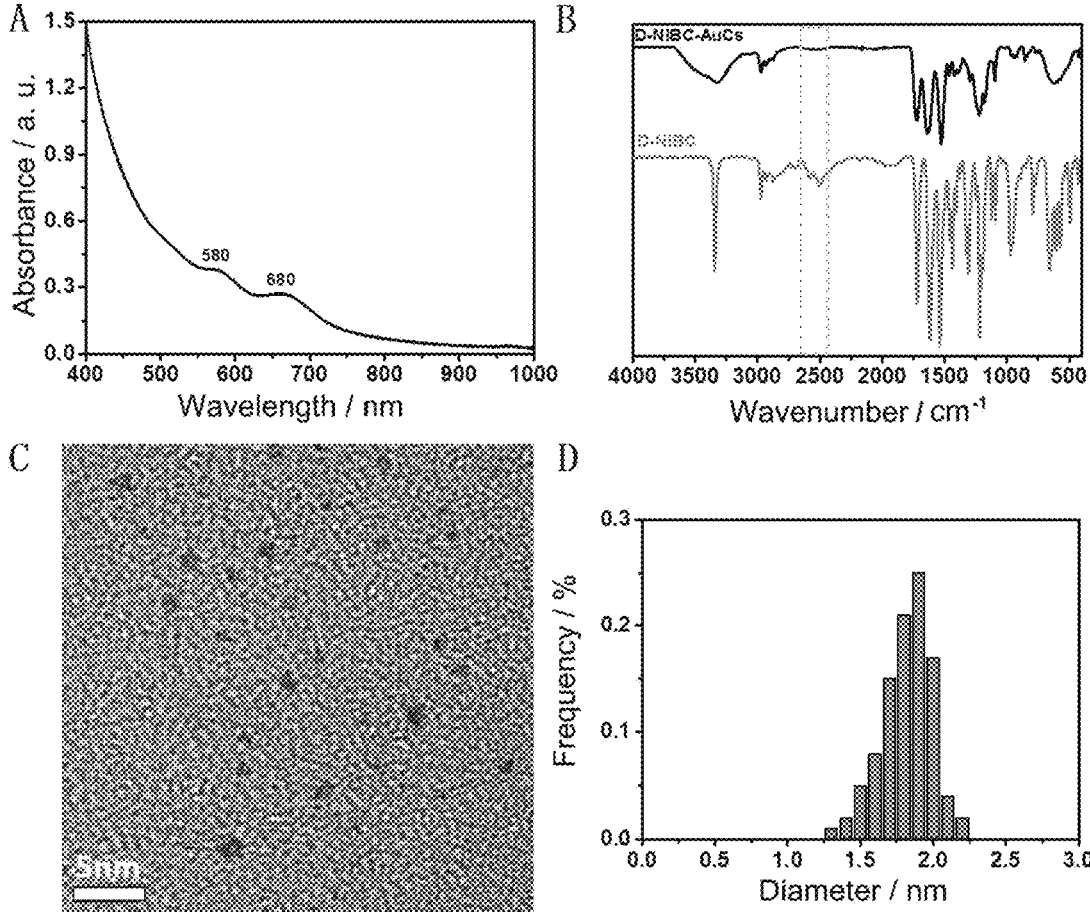
FIG. 8 shows UV, infrared, TEM, and particle size distribution diagrams of ligand D-NIBC-bound gold clusters (D-NIBC-AuCs).
Figure 9:
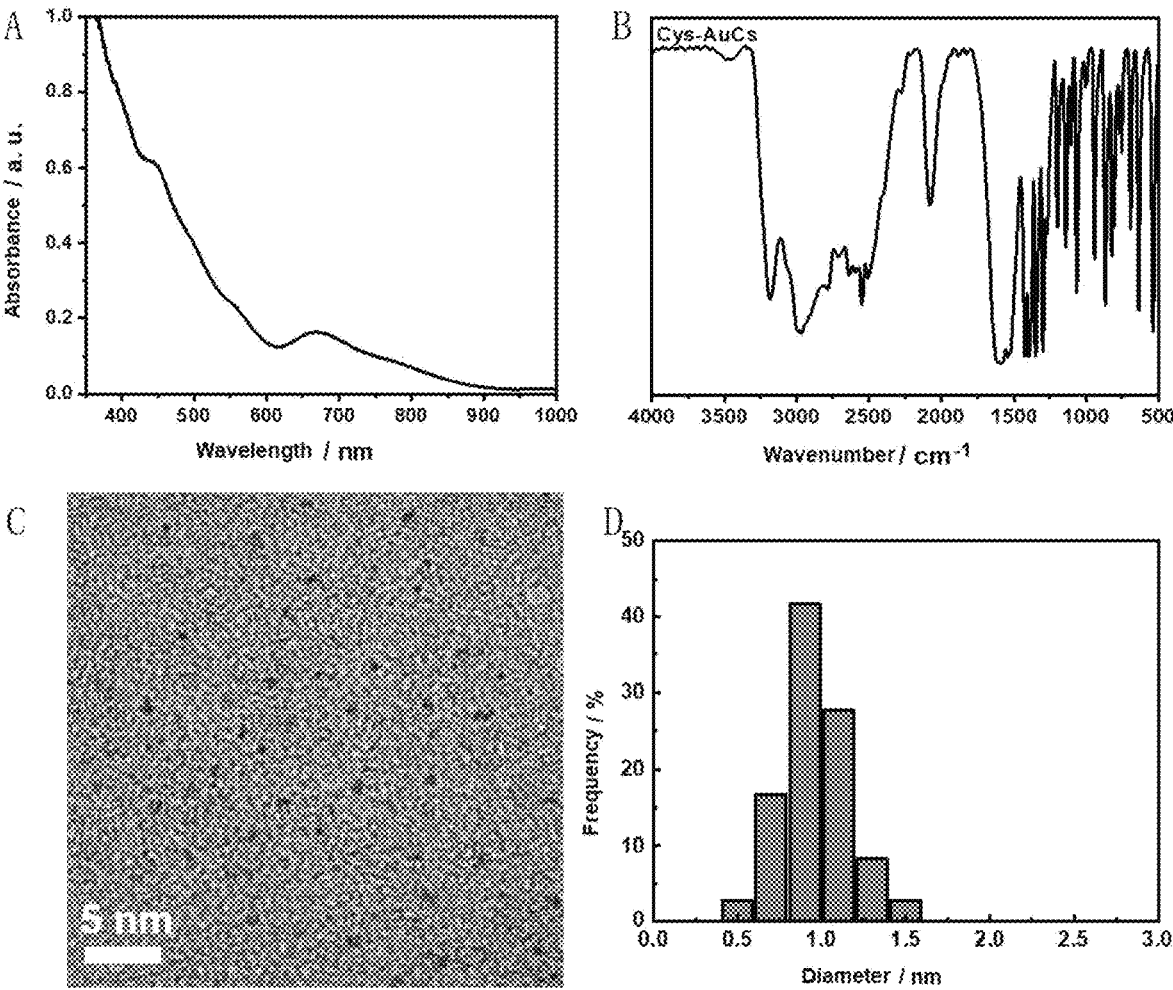
FIG. 9 shows UV, infrared, TEM, and particle size distribution diagrams of ligand L-cysteine-bound gold clusters (L-Cys-AuCs).

The samples listed in Table 1 are confirmed by the foregoing methods. The characteristics of six different ligand-bound AuCs are shown in FIG. 4 (CR-AuCs), in FIG. 5 (RC-AuCs), in FIG. 6 (Cap-AuCs) (Cap denotes 1-[(2S)-2-methyl-3-thiol-1-oxopropyl]-L-proline), in FIG. 7 (GSH-AuCs), in FIG. 8 (D-NIBC-AuCs), and in FIG. 9 (L-Cys-AuCs). FIGS. 4-FIG. 9 show UV spectra (panel A), infrared spectra (panel B), TEM images (panel C), and particle size distribution (panel D).

The results indicate that the diameters of AuCs bound with different ligands obtained from Table 1 are all smaller than 3 nm. Ultraviolet spectra also show disappearance of peak at 520±20 nm, and appearance of absorption peak in other positions. The position of the absorption peak could vary with ligands and particle sizes as well as structures. In certain situations, there is no special absorption peak, mainly due to the formation of AuCs mixtures with different particles sizes and structures or certain special AuCs that moves the position of absorption peak beyond the range of UV-vis spectrum. Meanwhile, Fourier transform infrared spectra also show the disappearance of ligand thiol infrared absorption peak (between the dotted lines in panel B of FIGS. 4-8), while other infrared characteristic peaks are all retained, suggesting that all ligand molecules have been successfully bound to gold atoms to form ligand-bound AuCs, and the present invention has successfully obtained AuCs bound with the ligands listed in Table 1.

TABLE 1

Preparation parameters of AuCs bound with different ligands in the present invention

| | | Parameter | | | |
|---|---|---|---|---|---|
| Ligand | Solvent used for solution B | Feed ratio between HAuCl$_4$ and ligand | Time of reaction in an ice bath under stirring before addition of NaBH$_4$ | Mole ratio between HAuCl$_4$ and NaBH4 | Time of reaction in an ice bath under stirring after addition of NaBH$_4$ |
| 1 L-cysteine | Acetic acid | 1:3 | 2 h | 1:2 | 0.5 h |
| 2 D-cysteine | Acetic acid | 1:3 | 2 h | 1:2 | 0.5 h |
| 3 N-acetyl-L-cysteine | Ethanol | 1:4 | 1 h | 1:1 | 0.5 h |
| 4 N-acetyl-D-cysteine | Ethanol | 1:4 | 1 h | 1:1 | 0.5 h |
| 5 L-NIBC | Water | 1:4 | 0.5 h | 1:2 | 0.5 h |
| 6 D-NIBC | Water | 1:4 | 0.5 h | 1:2 | 0.5 h |
| 7 Other cysteine derivatives | Soluble solvent | 1:(0.1~100) | 0.5 h~24 h | 1:(0.1~100) | 0.1~24 h |
| 8 CR | Water | 1:4 | 22 h | 2:1 | 0.5 h |
| 9 RC | Water | 1:4 | 20 h | 2:1 | 0.5 h |
| 10 HC | Water | 1:3 | 12 h | 1:2 | 2 h |
| 11 CH | Ethanol | 1:4 | 16 h | 1:3 | 3 h |
| 12 GSH | Water | 1:2 | 12 h | 1:1 | 3 h |
| 13 KCP | Water | 1:3 | 15 h | 1:2 | 1 h |
| 14 PCR | Water | 1:4 | 16 h | 1:3 | 2 h |
| 15 GSCR | Water | 1:4 | 16 h | 1:3 | 1.5 h |
| 16 GCSR | Water | 1:3 | 12 h | 1:2 | 2 h |
| 17 Other oligopeptides containing cysteine | Soluble solvent | 1:(0.1~100) | 0.5 h~24 h | 1:(0.1~100) | 0.1~24 h |
| 18 1-[(2S)-2-methyl-3-thiol-1-oxopropyl]-L-proline | Water | 1:8 | 2 h | 1:7 | 1 h |
| 19 Mercaptoethanol | Ethanol | 1:2 | 2 h | 1:1 | 1 h |
| 20 Thioglycollic acid | Acetic acid | 1:2 | 2 h | 1:1 | 1 h |
| 21 Thiophenol | Ethanol | 1:5 | 5 h | 1:1 | 1 h |
| 22 D-3-trolovol | Water | 1:2 | 2 h | 1:1 | 1 h |
| 23 N-(2-mercaptopropionyl)-glycine | Water | 1:2 | 2 h | 1:1 | 1 h |
| 24 Dodecyl mercaptan | Methanol | 1:5 | 5 h | 1:1 | 1 h |
| 25 Other compounds containing thiol | Soluble solvent | 1:(0.01~100) | 0.5 h~24 h | 1:(0.1~100) | 0.1~24 h |

Embodiment 3

3.1 Materials and animals

3.1.1 Testing Sample

A-01: ligand L-NIBC-bound gold clusters (L-NIBC-AuCs), 0.9±0.2 nm.

A-02: ligand L-NIBC-bound gold clusters (L-NIBC-AuCs), 1.9±0.5 nm.

B-01: ligand L-Cys-bound gold clusters (L-Cys-AuCs), 1.0±0.2 nm.

B-02: ligand L-Cys-bound gold clusters (L-Cys-AuCs), 1.7±0.3 nm.

C: L-NIBC-modified nanoparticles (L-NIBC-AuNPs), 6.3±1.5 nm

All testing samples were prepared following the above described method with slight modification, and their quality was characterized using the above described methods.

3.1.2 Positive control sample

Sorafenib.

3.3 Administration

After the successful modeling, the mice in the positive control group were given intragastrically 25 mg/kg sorafenib; the mice in the low or high dose groups of A-01, A-02, B-01 and B-02 were given by intraperitoneal injection at 2.5 or 10 mg/kg respectively of the corresponding test material; the mice in the C high dose group were given by intraperitoneal injection at a dose of 40 mg/kg of C; and the mice in the blank control group and the model group were given intraperitoneally physiological saline at 10 mL/kg. The administration was once a day for 20 consecutive days.

3.4 Biochemical testing

After the administration was completed, blood was collected from mouse orbit, and sera were obtained for biochemical testing of albumin (ALbumin, ALB), total bilirubin (TBil), alanine Alanine aminotransferase (ALT), aspartate aminotransferase (AST) and monoamine oxidase (MAO) using Zhongsheng Beikong Kit and biochemical analyzer (Siemens). The detection method was performed in strict accordance with the kit instructions.

TABLE 2 shows the product information of kits used for biochemical testing

| Serial number | Kit name | abbreviation | registration number |
|---|---|---|---|
| 1 | Albumin Test Kit (Bromocresol Green Method) | ALB | Beijing Food and Drug administration Device (Permit) 2014 No. 2401133 |
| 2 | Total bilirubin test kit (vanadate oxidation method) | TBil | Beijing Food and Drug administration Device (Permit) 2014 No. 2401140 |
| 3 | Alanine aminotransferase test kit (alanine substrate method) | ALT | Beijing Food and Drug administration Device (Permit) 2014 No. 2401158 |
| 4 | Aspartate aminotransferase test kit (aspartic acid substrate method) | AST | Beijing Food and Drug administration Device (Permit) 2014 No. 2401157 |
| 5 | Monoamine oxidase test kit (glutamic acid dehydrogenase method) | MAO | Beijing Food and Drug administration Device (Permit) 20162401129 |

3.1.3 Animals for experiments and groups

120 SPF male C57BL/6N mice, 6-8 weeks old and 16-20 g body weight, were purchased from Beijing Huafukang Experimental Animal Technology Co., Ltd. (production license number: SOCK (Jing) 2019-0008). According to body weight, they were randomly divided into 12 groups (n=10): blank control group, model group, positive control group, A-01 low dose group, A-01 high dose group, A-02 low dose group, A-02 high dose group, B-01 low-dose group, B-01 high-dose group, B-02 low-dose group, B-02 high-dose group, and C high-dose group.

3.2 Modeling protocol

Except for the blank control group, liver cirrhosis model of mice in other groups was prepared by the method of carbon tetrachloride ($CCl_4$)-induction treatment. The modeling protocol was as follows: (1) Each mouse was intraperitoneally injected with 10% $CCl_4$ (diluted with olive oil) at 7 μL/g body weight, twice a week for a total of 8 weeks; mice of the blank control group were injected intraperitoneally with the same amount of olive oil solvent. (2) from the 6th week, two mice were selected and killed 48 hours after the last injection every week. The appearance of the liver was observed. After the appearance was in line with the characteristics of cirrhosis (the 8th week), the liver tissue was fixed with formalin. HE staining and Masson staining were used to evaluate the model of cirrhosis.

3.5 Pathological examination

3.5.1 HE staining

After euthanasia, the mouse liver tissue samples were fixed with 4% paraformaldehyde fixative for more than 48 h. After fixation, the liver samples were dehydrated with alcohol gradient and treated with xylene and ethanol. Then, the liver tissues were then dipped in wax and embedded. After the embedded material being trimmed, attached, and repaired, the liver tissues were sliced with a paraffin microtome, and the slices were with a thickness of 4 μm. The main process of HE staining is as follows: After baked in the oven at 65° C., the slices were treated with xylene and dehydrated with gradient ethanol. The slices were sequentially stained with hematoxylin, blue color-enhancing solution, and 0.5% eosin, then treated with gradient ethanol and xylene and sealed with neutral gum. The fibrosis of liver tissue was observed with a microscope.

3.5.2 Masson staining

After baked, mouse liver tissue slices were dewaxed and dehydrated. After chromizing, the nucleus was stained with Regaud's hematoxylin staining solution. After washing with water, the slices were stained with Masson's Ponceau Red Acidic Fuchsin, and the slices were dipped in a 2% glacial acetic acid aqueous solution and differentiated with a 1% phosphomolybdic acid solution. After directly stained with aniline blue or light green solution, the slices were dipped in a 0.2% glacial acetic acid aqueous solution for a while, then transparentized with 95% alcohol, anhydrous alcohol and xylene, and then sealed with neutral gum. Liver tissue was observed with a microscope.

3.6 Results 3.6.1 Successful Modeling

The livers of mice in the model group were divided into round or oval masses of different sizes by proliferating fibrous septa. The serum ALT, TBil, and AST indexes increased significantly compared to that of the blank control group, the serum ALB significantly decreased compared to the blank control group, and the MAO index was no significant difference from the control group, but the value also increased. All the above results suggest that this experimental modeling was successful.

3.6.2 Effects of test drugs on alanine aminotransferase (ALT), total bilirubin (TBil), aspartate aminotransferase (AST), monoamine oxidase (MAO) and albumin (ALB)

3.6.2.1 Test drugs A-01 and A-02

Figure 10:
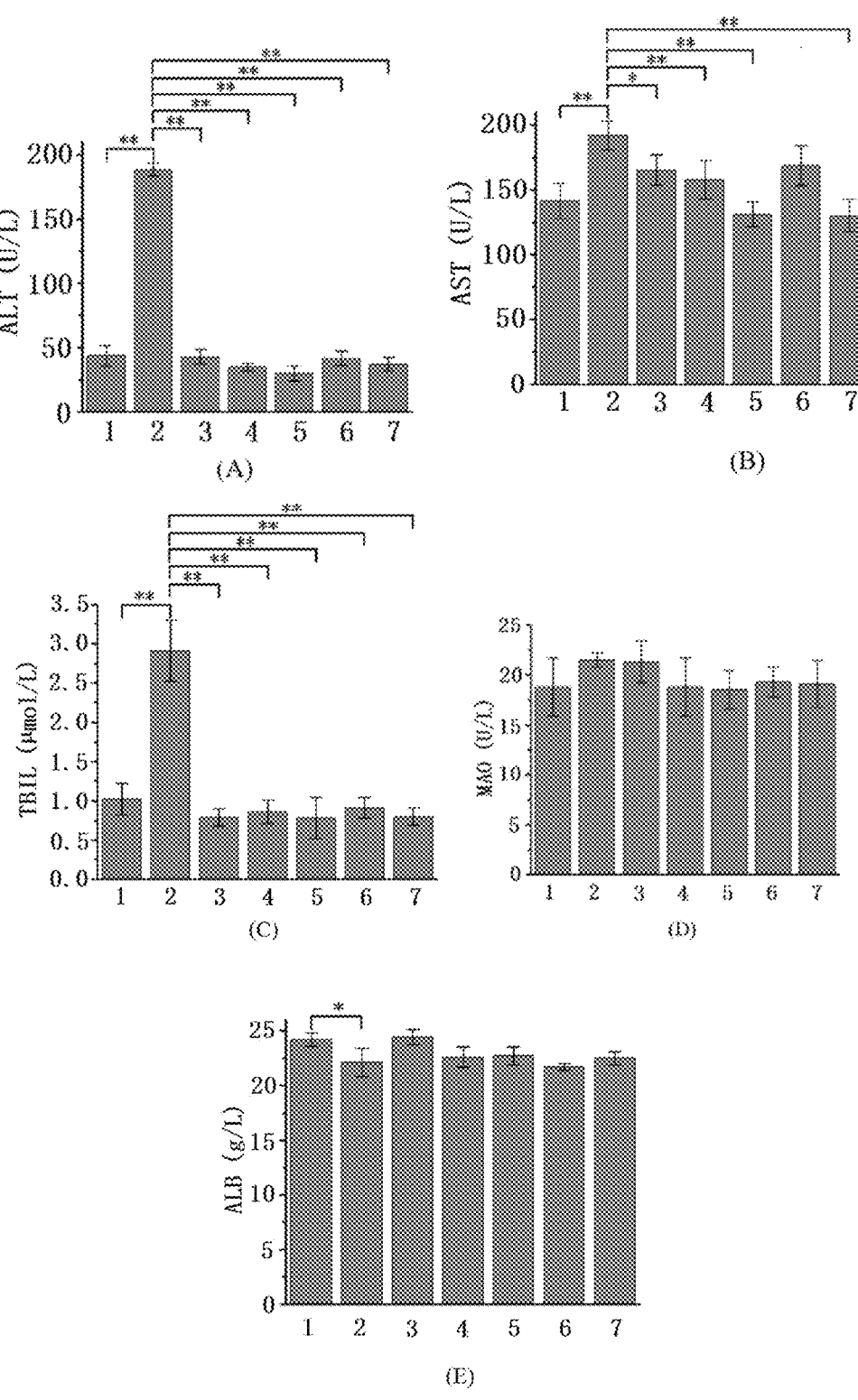
FIG. 10 presents bar graphs showing the effects of different doses of A-01 and A-02 on serum (A) ALT, (B) AST, (C) TBIL, (D) MAO and (E) ALB levels in cirrhotic model mice, where 1) denotes the blank control group, 2) the model group, 3) the positive group treated with sorafenib, 4) A-01 low dose group, 5) A-01 high dose group, 6) A-02 low dose group, and 7) A-02 high dose group.

As shown in FIG. 10A, the ALT activity of the model group is extremely significantly higher than that of the blank control group (increased from 43.5±8.1 U/L to 188.5±4.9 U/L; P<0.01), which indicates that liver functions of the cirrhotic model mice had pathological changes. After administration of A-01 and A-02 at high and low doses, the ALT activity of all treated groups decreased significantly (the highest is 41.5±5.4 U/L for A-02 low dose group; the lowest is 30.0±5.9 U/L for A-01 high dose group; and 42.8±5.4 U/L for positive control group), and returned to the similar level of the blank control group or even lower, which is significantly different from that of the model group (P<0.01).

As shown in FIG. 10B, the serum AST activity of the model group was significantly increased compared to the blank control group (increased from 141.9±13.5 U/L to 192.0±11.3 U/L; P<0.05). After the administration of A-01 and A-02, the AST activity of all treated groups decreased, where the high-dose A-01 and A-02 administration significantly reduced the AST activity (130±12.8 U/L for A-01 high dose group; 131.3±9.9 U/L for A-02 high dose group; both P<0.01), obviously superior to the positive control group (165.5±11.6 U/L).

As shown in FIG. 10C, the concentration of TBil of the model group was significantly higher than that of the blank control group (increased from 1.02±0.20 μmol/L to 2.91±0.39 μmol/L), and there was a significant difference from the blank control group (P<0.01). After administration of high and low doses of A-01 and A-02, the concentrations of TBil were all significantly reduced (the highest is 0.91±0.13 μmol/L; the lowest is 0.78±0.25 μmol/L); they are in the similar level of the blank control group, but are extremely significantly different from the model group (P<0.01).

As shown in FIG. 10D, the MAO activity of the model group is increased compared to the blank control group (18.8±2.9 U/L for blank control group; 21.5±0.7 U/L for model group), but there is no statistical difference, suggesting that the changes of the MAO activity in the cirrhosis mice induced by carbon tetrachloride are not significant. The administration of A-01 and A-02 did not significantly affect the MAO activity of all treated groups, but the MAO activity of all treated groups decreased (the highest is 19.3±1.5 U/L and the lowest is 18.5±1.9 U/L); they are in the similar to the level of the blank control group. In comparison, the MAO activity of the positive control group did not decrease (21.3±2.1 U/L). This result suggests that A-01 and A-02 may adjust the activity of MAO to the level of the blank control group, playing a role in the recovery of liver functions in cirrhosis mice.

As shown in FIG. 10E, the ALB level of the model group is significantly decreased compared to the blank control group (decreased from 24.2±0.6 g/L to 22.1±1.3 g/L), and there is a significant difference from the blank control group (P<0.05), showing that carbon tetrachloride administration may significantly decrease serum ALB levels. The administration of different doses of A-01 and A-02, and positive control d did not significantly affect the serum ALB levels.

The positive drug sorafenib significantly reduced the levels of ALT, AST, and TBIL but may not have a relief effect on cirrhotic mice for the MAO index. The results suggest that A-01 and A-02 have a repairing effect on liver function in cirrhotic mice, and the effect is better than that of the positive control drug.

3.6.2.2 Test drugs B-01 and B-02

Figure 11:
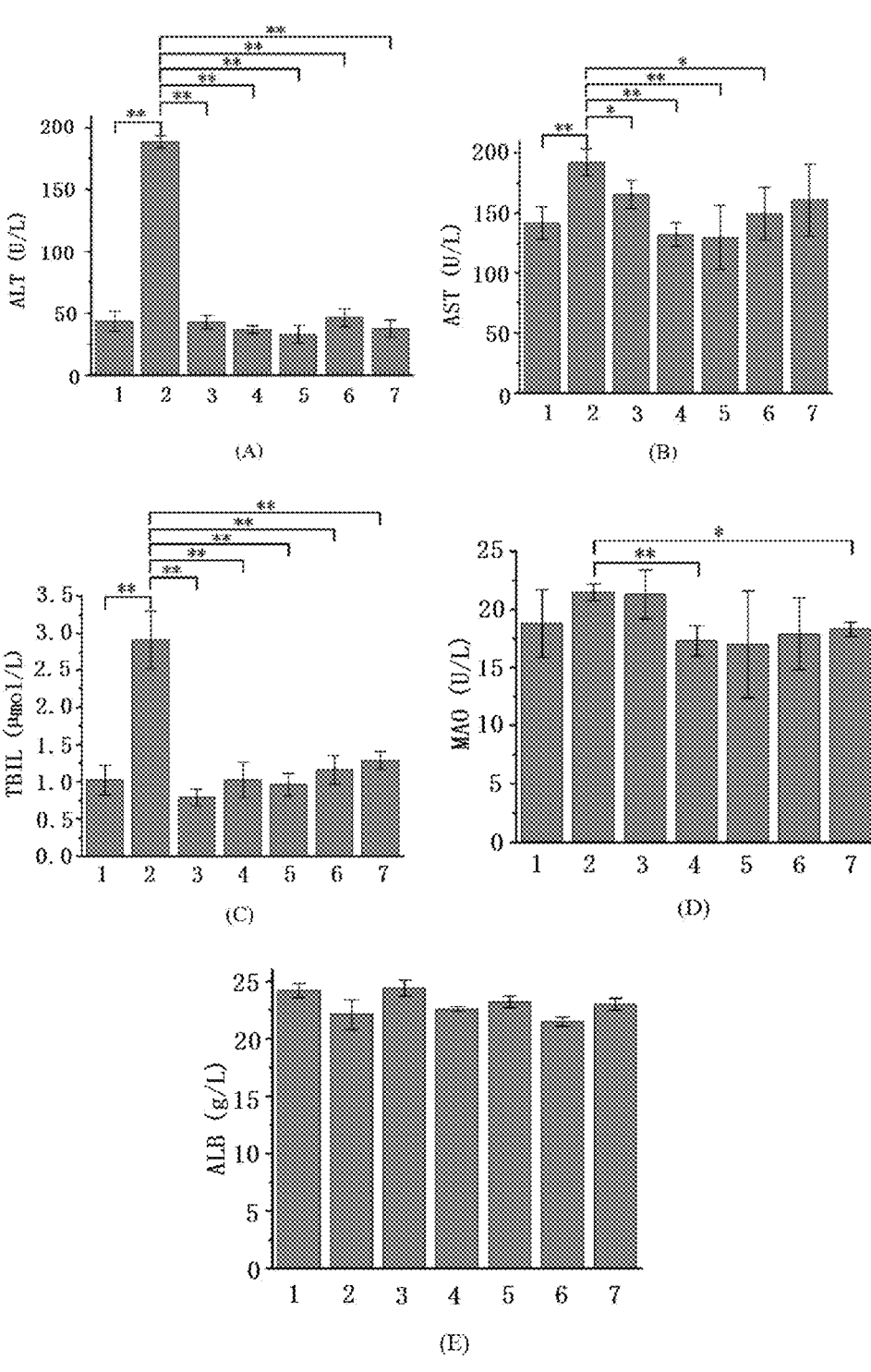
FIG. 11 presents bar graphs showing the effects of different doses of B-01 and B-02 on serum (A) ALT, (B) AST, (C) TBIL, (D) MAO and (E) ALB levels in cirrhotic model mice, where 1) denotes the blank control group, 2) the model group, 3) the positive group treated with sorafenib, 4) B-01 low dose group, 5) B-01 high dose group, 6) B-02 low dose group, and 7) B-02 high dose group.

As shown in FIG. 11A, the low and high doses of B-01 and B-02 could significantly reduce ALT activity (the highest is 46.3±7.4 U/L; the lowest is 33.0±7.1 U/L); they are in the level similar to the that of the blank control group, but significantly different from the model group (188.5±4.9 U/L; P<0.01).

As shown in FIG. 11B, compared with the model group (192.0±11.3 U/L), B-01 low or dose administration can significantly reduce AST activity to normal levels (132.3±10.0 U/L and 129.7±26.6 U/L respectively; P<0.01), and B-02 low dose administration can significantly reduce AST activity (149.6±21.8 U/L; P<0.05); they are in similar level to that of blank control group. But B-02 high-dose administration reduces AST activity to some extent, but there was no significant difference (P>0.05). In comparison, the positive drug sorafenib can also decrease the AST activity to 165.5±11.6 U/L (P<0.05), but the effect is not as good as the administration of B-01 low and high doses and B-02 low dose.

As shown in FIG. 11C, low and high doses of B-01 and B-02 all significantly reduced TBil (the highest is 1.28±0.12 μmol/L; the lowest is 0.96±0.15 μmol/L); they are in a level similar to that of the blank control group (1.02±0.20 μmol/L), but are significantly different from the model group (2.91±0.39 μmol/L; P<0.01).

As show in FIG. 11D, compared with the model group (21.5±0.7 U/L), B-01 low dose (17.3±1.3 U/L; P<0.01) and B-02 high dose (18.3±0.6 U/L; P<0.05) significantly reduced serum MAO levels to the blank control group (18.8±2.9 U/L), but positive control drug has no effect on the serum level of MAO (21.3±2.1 U/L).

As shown in FIG. 11E, administration of test drugs and positive control drug had no significant effect on ALB levels.

The above results show that B-01 and B-02 significantly reduce the levels of ALT, AST, TBIL and MAO, and have a certain dose-dependent effect on the liver function recovery of cirrhotic mice, and their effects are at least in some indicators better than the positive control drugs.

3.6.2.3 Test drugs C

Figure 12:
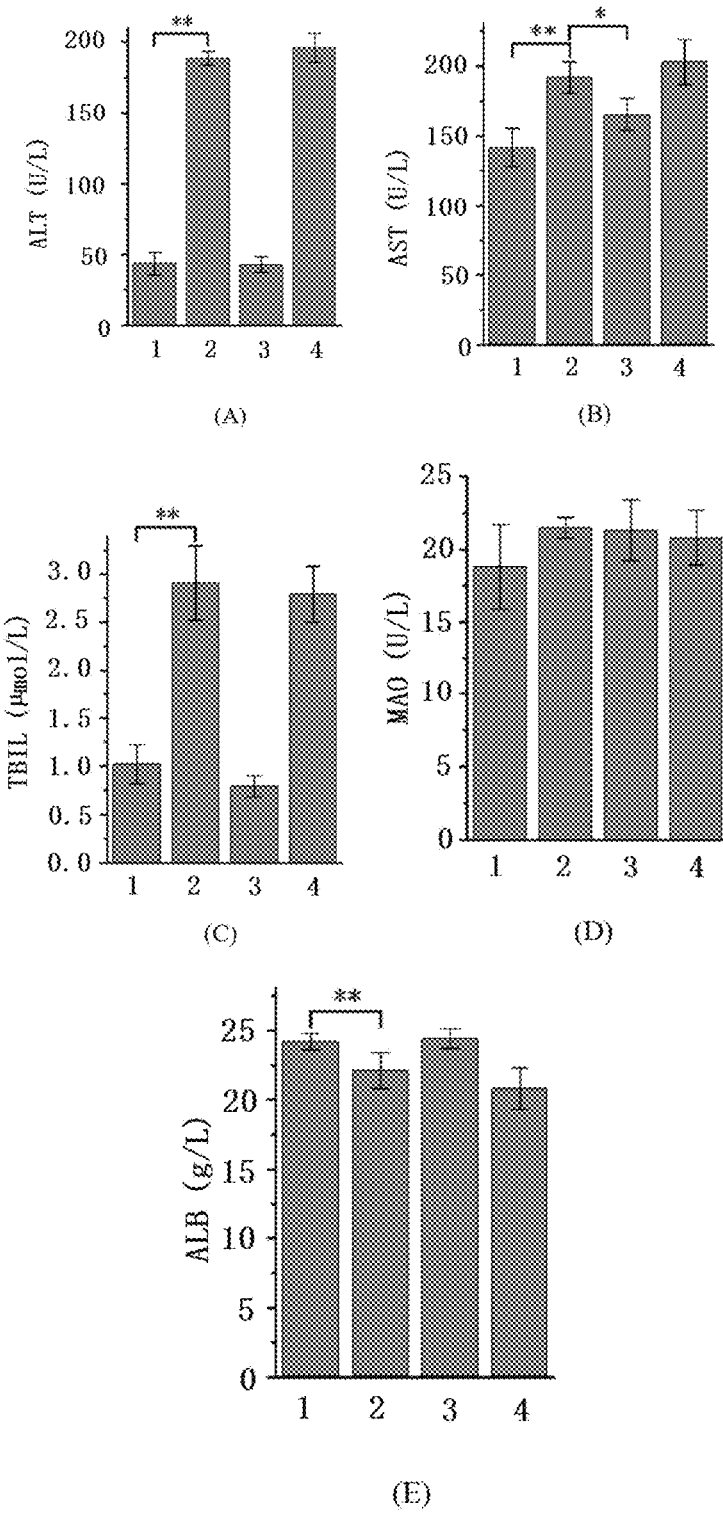
FIG. 12 presents bar graphs showing the effects of high dose C on serum (A) ALT, (B) AST, (C) TBIL, (D) MAO and (E) ALB levels in cirrhotic model mice, where 1) denotes the blank control group, 2) the model group, 3) the positive group treated with sorafenib, 4) drug C high dose group.

As shown in FIG. 12, compared with the model group, high-dose drug C administration has no significant improvement on the levels of (A) ALT, (B) AST, (C) TBIL, (D) MAO, and (E) ALB compared to the model control group, and there is even a certain deterioration trend, suggesting that the drug C is ineffective in improving the liver functions of cirrhotic mice and may be toxic.

3.6.3 Pathological analyses

Liver cirrhosis is pathologically characterized by diffuse fibrosis of the liver tissue and formation of pseudolobules.

Figure 13:
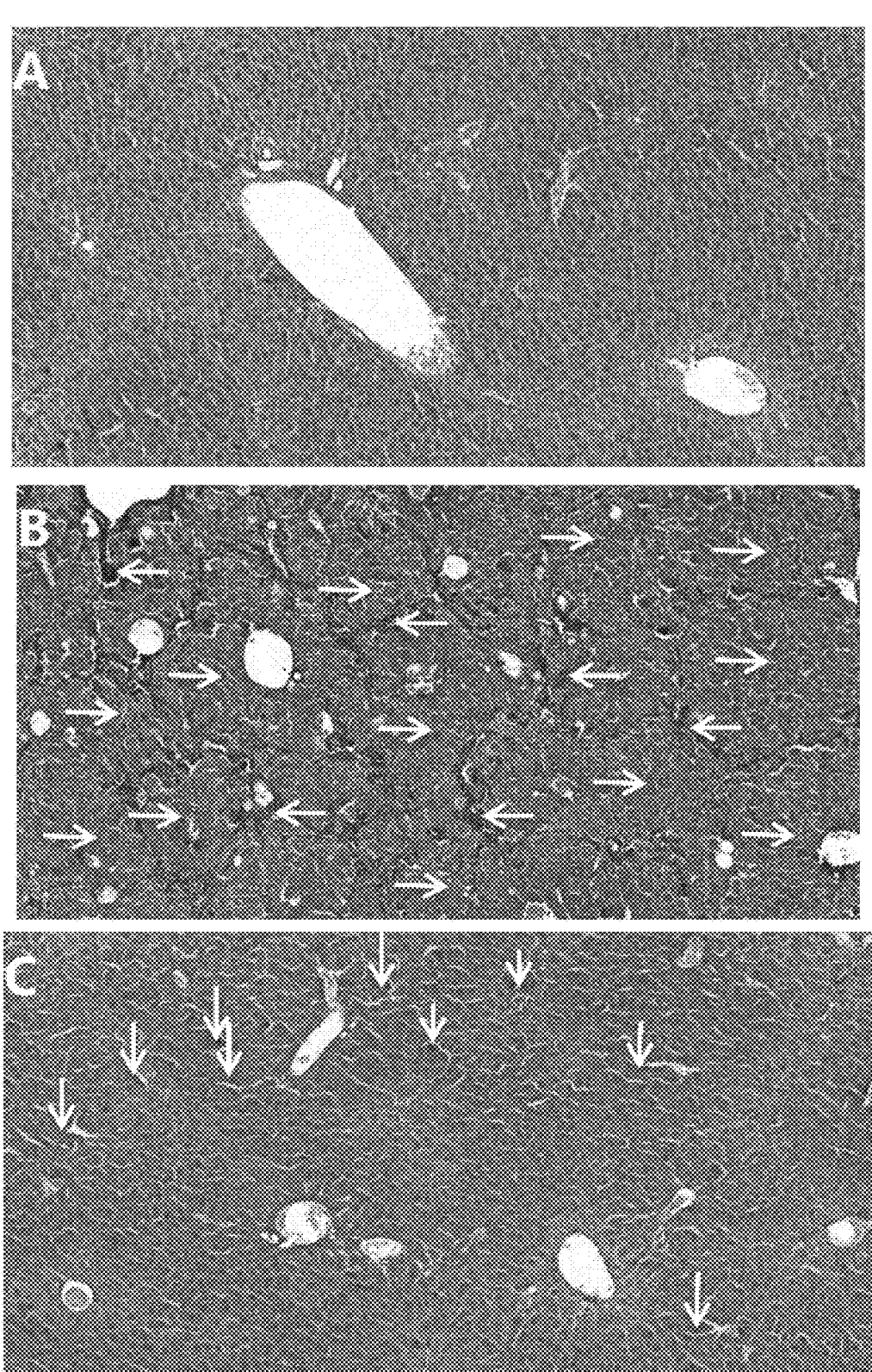
FIG. 13 presents HE staining images: (A) the blank control group; (B) the model group; (C) the positive control group; (D) A-01 low dose group; (E) A-01 high dose group.
Figure 13:
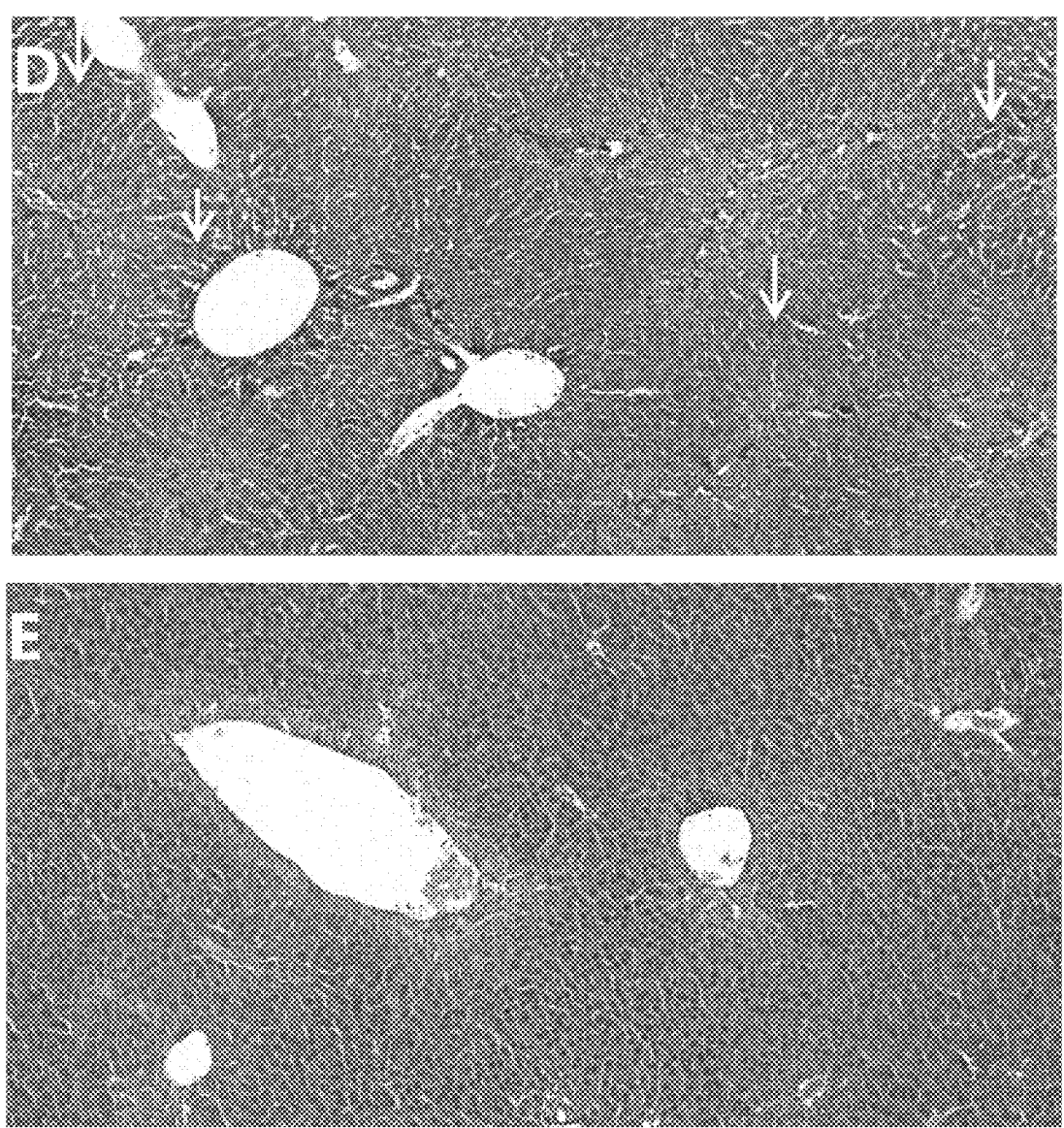

The results of HE staining pathological analyses showed that as shown in FIG. 13A, the normal liver tissue from the mice of the blank control group had clear structure, intact liver lobules, neatly arranged hepatocytes, radial arrangement being centered on the central vein, normal nucleus of hepatocytes, and only a small amount of fibrous tissue in the catchment area. As shown in FIG. 13B, in the liver tissue of the model group, the hepatocytes were disordered, balloon-like structures appeared, the hepatic lobules nearly disappeared, pseudolobules (as pointed to by right-orientated arrows in FIG. 13B) were abundantly formed, and a large number of proliferated protofibrils were present in the liver tissues, forming round- or oval-shaped fibrous septa (as pointed to by left-orientated arrows in FIG. 13B). As shown in FIG. 13C, compared with the model control group, the positive control group showed significant reduction of liver damages; the hepatocytes evidently have neat arrangement; fibrous hyperplasia, while increased, apparently reduced, not forming fibrous septa; pseudolobules nearly disappeared; but compared with normal liver tissues, the liver tissues in the positive control group showed apparent increases of inter-cellular gaps (as pointed to by downward-orientated arrows). Compared with the model control group, the 4 groups administered with gold clusters drugs (A-01, A-02, B-01 and B-02) showed that their hepatocytes significantly recovered from liver damages, as evidenced by apparent reduction of fibrous hyperplasia and pseudolobules, and that the recovery is dose-dependent to a certain extent.

FIG. 13D and FIG. 13E show the HE images that showed the effects of the exemplary A-01 lose and high dose drug administration respectively on the recovery of liver damages. As shown in FIG. 13D, A-01 low dose drug administration group showed relatively neat arrangement of hepatocytes, near disappearance of pseudolobules, evident reduction of fibrous hyperplasia, but the inter-hepatocytes gaps, compared with normal liver tissues, are increased to a certain extent (as pointed to by downward-orientated arrows in FIG. 13D). As shown in FIG. 13E, in comparison with A-01 low dose drug administration group, A-01 high dose drug administration group had even better effects of reduction of liver damages, complete disappearance of pseudolobules, no observation of fibrous hyperplasia, no discernable increases of inter-hepatocytes gaps, and no apparent difference from normal liver tissues. In conclusion, A-01 drug showed better effects on recovery of liver damages than the positive control drug.

The results from Masson staining provided the same conclusions as did the results of HE staining.

The other 3 drugs also showed similar effects of A-01 drug; no detailed description is needed.

In summary, the four test drugs A-01, A-02, B-01 and B-02 significantly reduced liver fibrous hyperplasia and liver pseudolobules. The test results of liver function indicators also showed the recovery of liver function. The most significant changes were alanine aminotransferase (ALT) and total bilirubin (TBil). Aspartate aminotransferase (AST) and monoamino oxidase (MAO) also recovered significantly, while albumin (ALB) did not change significantly. The four gold clusters drugs may significantly improve liver function and part of the liver pathological structure in cirrhotic mice, and the total effects are superior to the positive control drug sorafenib, providing experimental basis for further application in the future. However, drug C has no obvious therapeutic effect, and cannot be used for the treatment of liver cirrhosis.

Embodiment 4

4.1 Materials and animals 4.1.1 Testing Sample

D: ligand L-NAC-bound gold clusters (L-NAC-AuCs), 0.5-3 nm.

E: ligand CR-bound gold clusters (CR-AuCs), 0.5-3 nm.

F: ligand RC-bound gold clusters (RC-AuCs), 0.-3 nm.

All testing samples were prepared following the above described method with slight modification, and their quality was characterized using the above described methods.

4.1.2 Animals for experiments and groups

50 SPF male C57BL/6N mice, 6-8 weeks old and 16-20 g body weight, were purchased from Beijing Huafukang Experimental Animal Technology Co., Ltd. (production license number: SOCK (Jing) 2019-0008). According to body weight, they were randomly divided into 5 groups (n=10): blank control group, model group, D drug administration group, E drug administration group, and F drug administration group.

4.2 Modeling protocol

Except for the blank control group, liver cirrhosis model of mice in other groups was prepared by the method of carbon tetrachloride ($CCl_4$)-induction treatment. The modeling protocol was as follows: (1) Each mouse was intraperitoneally injected with 10% $CCl_4$ (diluted with olive oil) at 7 μL/g body weight, twice a week for a total of 8 weeks; mice of the blank control group were injected intraperitoneally with the same amount of olive oil solvent. (2) from the 6th week, two mice were selected and killed 48 hours after the last injection every week. The appearance of the liver was observed. After the appearance was in line with the characteristics of cirrhosis (the 8th week), the liver tissue was fixed with formalin. HE staining and Masson staining were used to evaluate the model of cirrhosis.

4.3 Administration

After the successful modeling, the mice in the three drug administration groups were given by intraperitoneal injection at a dose of 40 mg/kg respectively of the corresponding gold clusters drugs; and the mice in the blank control group and the model group were given intraperitoneally physiological saline at 10 mL/kg. The administration was once a day for 20 consecutive days.

4.4 Biochemical testing

The reagents and protocols were the same as described in section 3.4.

4.5 Results 4.5.1 Successful Modeling

The livers of mice in the model group were divided into round or oval masses of different sizes by proliferating fibrous septa. The serum ALT, TBil, and AST indexes increased significantly compared to that of the blank control group, the serum ALB significantly decreased compared to the blank control group, and the MAO index was no significant difference from the control group, but the value also increased. All the above results suggest that this experimental modeling was successful.

4.5.2 Effects of Test Drugs on Alanine Aminotransferase (ALT), Total Bilirubin (TBil), Aspartate Aminotransferase (AST), Monoamine Oxidase (MAO) and Albumin (ALB)

Figure 14:
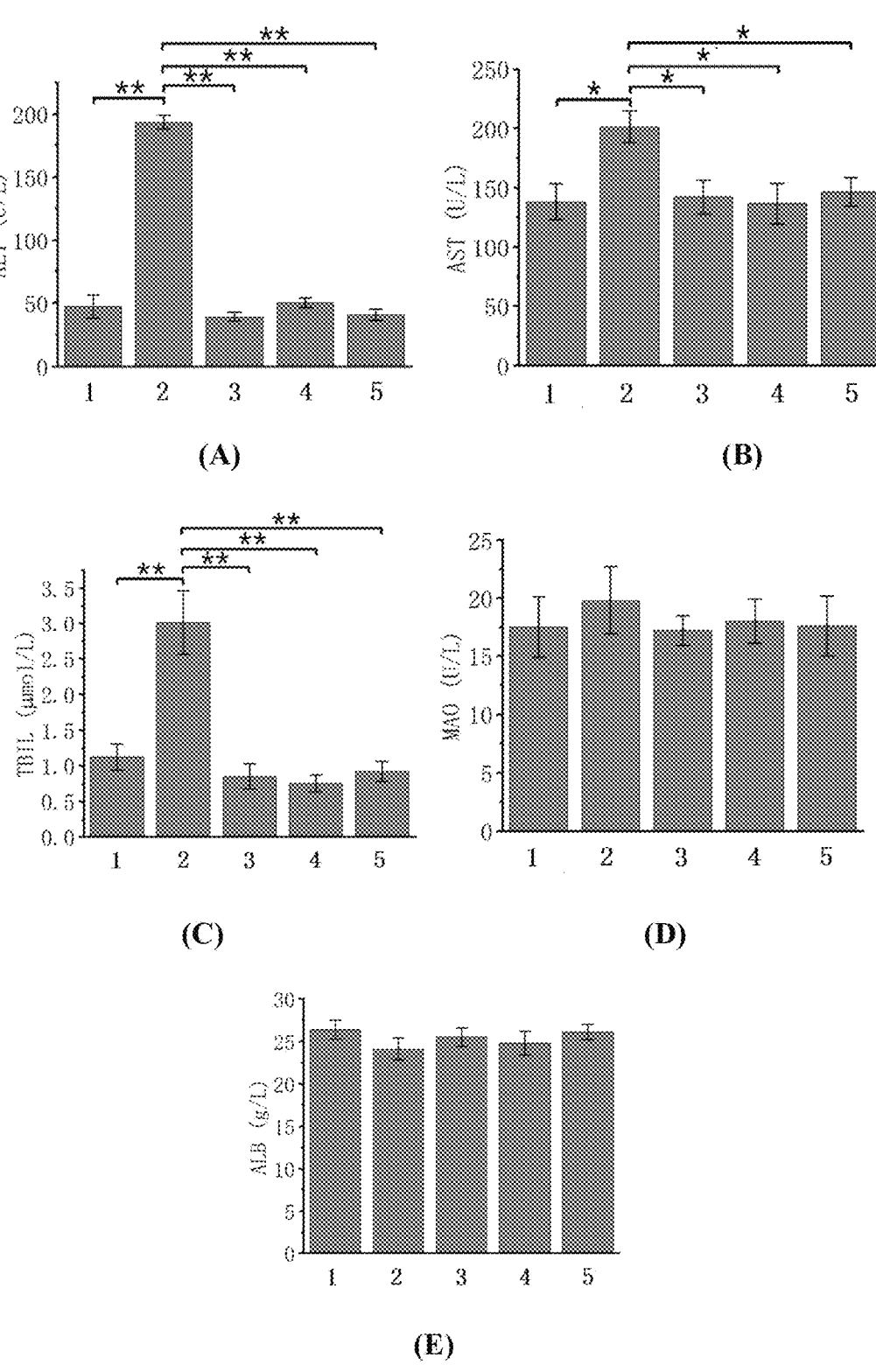
FIG. 14 presents bar graphs showing the effects of D, E and F drugs on serum (A) ALT, (B) AST, (C) TBIL, (D) MAO and (E) ALB levels in cirrhotic model mice, where 1) denotes the blank control group, 2) the model group, 3) D drug group, 4) E drug group, and 5) F drug group.

As shown in FIG. 14A, the ALT activity of the model group is extremely significantly higher than that of the blank control group (P<0.01, **), which indicates that liver functions of the cirrhotic model mice had pathological changes. After administration of D, E or F drugs, the ALT activity of all treated groups decreased significantly, and returned to the similar level of the blank control group, which is significantly different from that of the model group (P<0.01).

As shown in FIG. 14B, the AST activity of the model group is significantly higher than that of the blank control group (P<0.05, *). After administration of D, E or F drugs, the AST activity of all treated groups decreased significantly (P<0.05, *).

As shown in FIG. 14C, the TBil concentration of the model group is significantly higher than that of the blank control group (P<0.01, ). After administration of D, E or F drugs, the TBil concentration of all treated groups decreased significantly to the level of the blank control group, but are significantly different than that of the model control group (P<0.01, ).

As shown in FIG. 14D, the MAO activity of the model group was increased compared to the blank control group, but there is no statistical difference (P>0.5), suggesting that the changes of the MAO activity in the cirrhosis mice induced by carbon tetrachloride are not significant. The administration of D, E or F drugs did not significantly affect MAO activity, but the MAO activity of all drug administration groups decreased to the level of the blank control group.

As shown in FIG. 14E, the ALB concentration of the model group is decreased in comparison with that of the blank control group, but the difference is not significant (P>0.05). However, the administration of D, E or F drugs increased the serum ALB concentration, but the difference is not significant (P>0.05).

In summary, the three gold clusters drugs D, E and F significantly improved liver function. Alanine aminotransferase (ALT) and total bilirubin (TBil) showed the most significant changes, aspartate aminotransferase (AST) and monoamino oxidase (MAO) showed evident recovery, and albumin (ALB) was also improved, while not significantly. These results provide experimental basis for further application in the future.

Other sized L-Cys-AuCs, L-NIBC-AuCs, L-NAC-AuCs, CR-AuCs, RC-AuCs, and other ligand-bound AuCs with different sizes also have the similar effects, while their effects vary to certain extents. They would not be described in detail here.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the scope of the present invention. Accordingly, the scope of the present invention is defined by the appended claims and is supported by the foregoing description.

The invention claimed is:

1. A method for treating liver cirrhosis in a subject, wherein the method comprises:

administering a composition to the subject with liver cirrhosis;

wherein the composition comprises a ligand-bound gold cluster as a therapeutically active ingredient; and a pharmaceutically acceptable excipient;

wherein the ligand-bound gold cluster comprises:

a gold core; and a ligand bound to the gold core;

wherein the gold core has a diameter in the range of 0.5-3 nm; and wherein the ligand is selected from the group consisting of L-cysteine, N-isobutyryl-L-cysteine (L-NIBC), and N-acetyl-L-cysteine (L-NAC), and wherein theD-cysteine and its derivatives are selected from the group consisting of D-cysteine, N-isobutyryl-D-cysteine (D-NIBC), N-acetyl-D-cysteine (D-NAC), cysteine-containing oligopeptides and their derivatives, and other thiol-containing compounds.

2. The method of claim 1, wherein the gold core has a diameter in the range of 0.5-2.6 nm.

3. The method of claim 1, wherein the cysteine-containing oligopeptides and their derivatives are cysteine-containing dipeptides, cysteine-containing tripeptides or cysteine-containing tetrapeptides.

4. The method of claim 3, wherein the cysteine-containing dipeptides are selected from the group consisting of L(D)-cysteine-L(D)-arginine dipeptide (CR), L(D)-arginine-L(D)-cysteine dipeptide (RC), L(D)-histidine-L(D)-cysteine dipeptide (HC), and L(D)-cysteine-L(D)-histidine dipeptide (CH).

5. The method of claim 3, wherein the cysteine-containing tripeptides are selected from the group consisting of glycine-L(D)-cysteine-L(D)-arginine tripeptide (GCR), L(D)-proline-L(D)-cysteine-L(D)-arginine tripeptide (PCR), L(D)-lysine-L(D)-cysteine-L(D)-proline tripeptide (KCP), and L(D)-glutathione (GSH).

6. The method of claim 3, wherein the cysteine-containing tetrapeptides are selected from the group consisting of glycine-L(D)-serine-L(D)-cysteine-L(D)-arginine tetrapeptide (GSCR), and glycine-L(D)-cysteine-L(D)-serine-L(D)-arginine tetrapeptide (GCSR).

7. The method of claim 1, wherein the other thiol-containing compounds are selected from the group consisting of 1-[(2S)-2-methyl-3-thiol-1-oxopropyl]-L(D)-proline, thioglycollic acid, mercaptoethanol, thiophenol, D-3-trolovol, N-(2-mercaptopropionyl)-glycine, and dodecyl mercaptan.

* * * * *